United States Patent
Gokaraju et al.

(10) Patent No.: US 7,026,518 B2
(45) Date of Patent: Apr. 11, 2006

(54) RESVERATROL ANALOGS

(75) Inventors: Ganga Raju Gokaraju, Andhra Pradesh (IN); Rama Raju Gokaraju, Andhra Pradesh (IN); Venkata Subbaraju Gottumukkala, Andhra Pradesh (IN); Venkateswarlu Somepalli, Andhra Pradesh (IN)

(73) Assignee: Laila Impex, Andhra Pradesh (IN)

( * ) Notice: Subject to any disclaimer, the term of this patent is extended or adjusted under 35 U.S.C. 154(b) by 53 days.

(21) Appl. No.: 10/486,774

(22) PCT Filed: Jun. 25, 2002

(86) PCT No.: PCT/IN02/00138

§ 371 (c)(1),
(2), (4) Date: Feb. 13, 2004

(87) PCT Pub. No.: WO04/000302

PCT Pub. Date: Dec. 31, 2003

(65) Prior Publication Data

US 2004/0209951 A1    Oct. 21, 2004

(51) Int. Cl.
    *C07C 39/12* (2006.01)
(52) U.S. Cl. .................................................. 568/729
(58) Field of Classification Search ............... 514/544, 514/551, 733; 560/68, 75, 138; 569/729
    See application file for complete search history.

(56) References Cited

U.S. PATENT DOCUMENTS

| 6,124,364 A | 9/2000 | Breton et al. ............... 514/733 |
| 2002/0183400 A1 | 12/2002 | Baldo et al. ................ 514/733 |

OTHER PUBLICATIONS

Matsumada, H. et al.; "Antioxident Constituents from Rhubarb: Structural Requirements of Stilbenes for the Activity and Structures of Two New Anthraquinone Glucosides" *Bioorganic & Medicinal Chemistry*. 2001, vol. 9, No. 1, pp. 41-50.

*Primary Examiner*—Paul A. Zucker
(74) *Attorney, Agent, or Firm*—Ladas & Parry LLP

(57) ABSTRACT

Novel resveratrol analogs that are potent antioxidants. The resveratrol analogs are illustrated in the following general formula I:

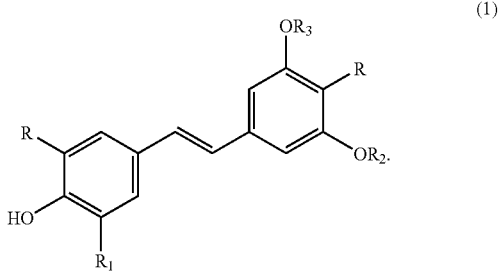

13 Claims, 1 Drawing Sheet

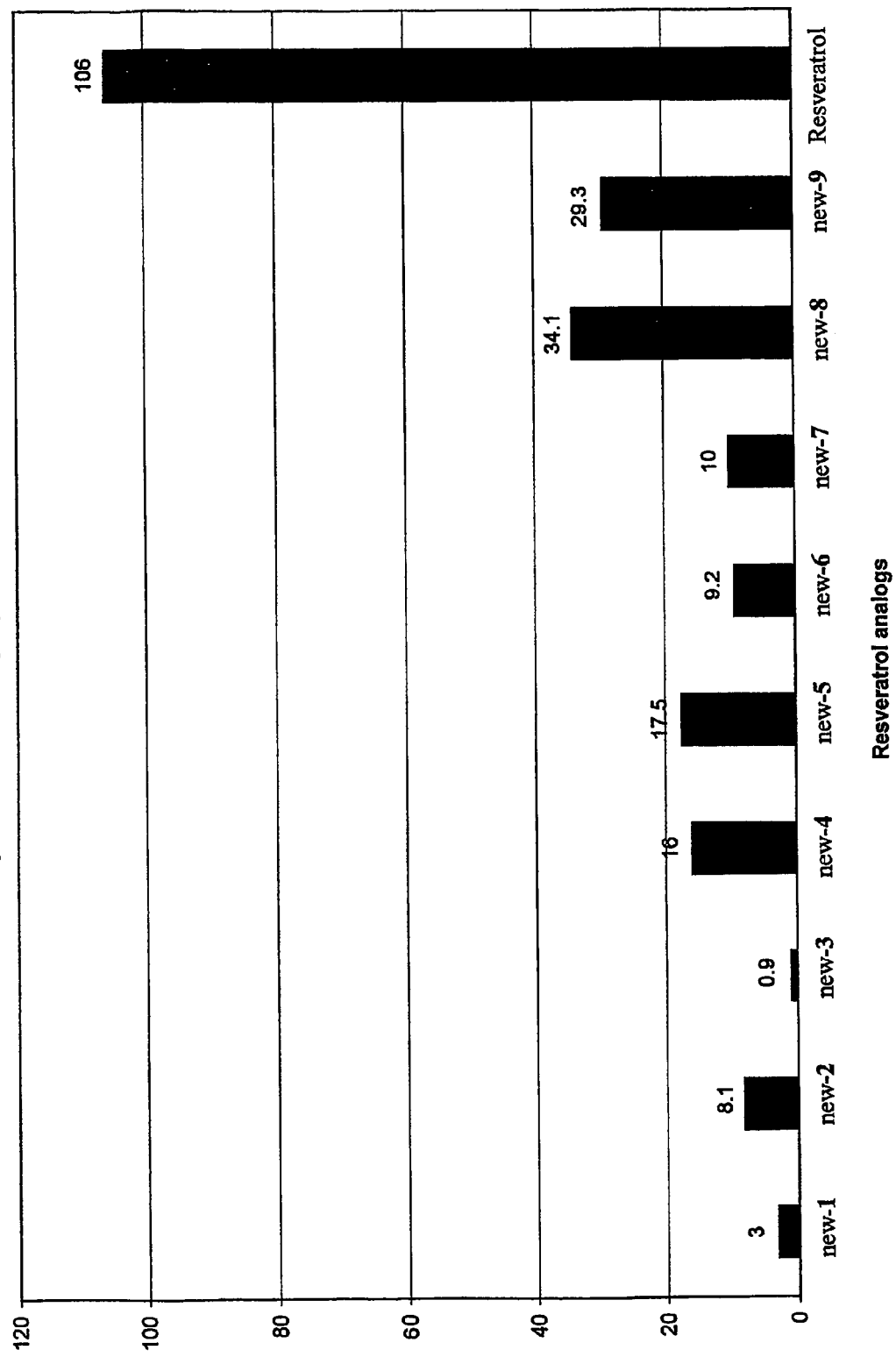

RESVERATROL ANALOGS

This invention relates to novel resveratrol analogs which are potent antioxidants.

TECHNICAL FIELD

Free radicals play a major role in the progression of a wide range of pathological disorders such as brain dysfunction, cancer, cardiovascular disease and inflammation. Free radicals are also found to be responsible for deterioration of food articles during processing and storage. Addition of antioxidants and free radical scavengers to processed foods reduce the harmful effects of free radicals. Antioxidants and superoxide scavengers are also found to control the harmful effect of free radicals in biological systems.

3,4',5-trihydroxystilbene commonly known as resveratrol is found in grapes. Resveratrol is found to exihibit antioxidative and antimutagenic properties. Resveratrol is also an inducer of phase II drug metabolizing enzymes. In humans, resveratrol consumption is found to inhibit peroxidation of plasma low density lipoprotein and this effect has been proposed to protect against the development of atherosclerosis. The above referenced bioprotective properties of resveratrol are attributed to the presence of phenolic groups in its structure. Naturally occurring resveratrol of the formula given below is found to exhibit better bioprotective activity than the corresponding methylated derivatives.

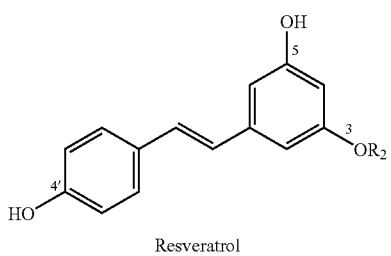

Resveratrol

BACKGROUND ART

Antioxidant and superoxide scavenging properties of resveratrol have been scientifically established. Efforts are being made to synthesise structural analogs of resveratrol for evaluation of their relative antioxidant potentials.

BRIEF DESCRIPTION OF THE DRAWINGS

FIG. I shows the superoxide scavenging activity of various resveratrol analogs.

DISCLOSURE OF THE INVENTION

It has now been found that novel resveratrol analogs of the general formula I

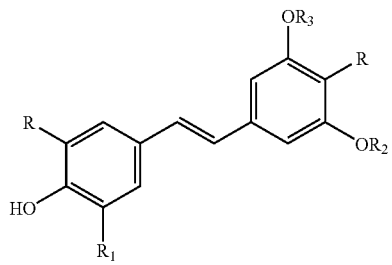

show improved and better antioxidative action than the naturally occuring resveratrol. Enhanced activity of these compounds may be due to the presence of catechol, pyrogallol moieties or a combination of these in their structure.

This invention relates to novel resveratrol analogs of the formula I

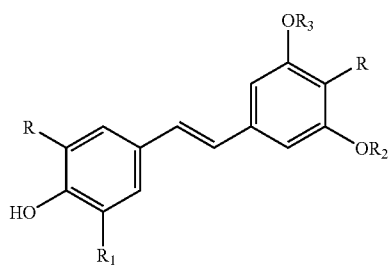

wherein R, $R_1$, $R_2$ and $R_3$ are:
1. R=OH, $R_1$=$R_2$=$R_3$=H;
2. R=OH, $R_1$=Br, $R_2$=$R_3$=H;
3. R=$R_1$=OH, $R_2$=$R_3$=H;
4. R=$R_1$=$R_3$=H, $R_2$=3,4,5-trihydroxybenzoyl;
5. R=$R_1$=H, $R_2$=$R_3$=3,4,5-trihydroxybenzoyl;
6. R=$R_1$=$R_3$=H, $R_2$=3,4-dihydroxycinnamoyl;
7. R=$R_1$=$R_3$=H, $R_2$=3,4,5-trihydroxycinnamoyl;
8. R=$R_1$=$R_3$=H, $R_2$=—$CH_2CH_2N(CH_3)_2$;
9. R=$R_1$=$R_3$=H, $R_2$=—$COCH_2NH_2.HCl$ Prefered compounds of the invention are
(1) 5-[(1E)-2-(3,4-dihydroxyphenyl)vinyl]-benzene1,2,3-triol, 1
(2) 5-[(1E)-2-(5-Bromo-3,4-dihydroxyphenyl)vinyl]-benzene1,2,3-triol, 2
(3) 5-[(1E)-2-(3,4,5-trihydroxyphenyl)vinyl]-benzene1,2,3-triol, 3
(4) 5-[(1E)2-(4-hydroxyphenyl)vinyl]-3-hydroxyphenyl 3,4,5-trihydroxybenzoate, 4
(5) 3-[(1E)-2-(4-hydroxyphenyl)vinyl]-5-(3,4,5trihydroxyphenylcarbonyloxy)-phenyl 3,4,5-trihydroxybenzoate, 5
(6) 5-[(1E)-2-(4-hydroxyphenyl)vinyl]-3-hydroxyphenyl (2E)-3(3,4-dihydroxyphenyl) prop-2-enoate, 6
(7) 5-[(1E)-2-(4-hydroxyphenyl)vinyl]-3-hydroxyphenyl (2E)3(3,4,5-trihydroxyphenyl) prop-2-enoate, 7
(8) 3-[(1E)-2-(4-hydroxyphenyl)vinyl]-5-[2-(dimethylamino)ethoxy] phenol, 8
(9) 5-[(1E)-2-(4-hydroxyphenyl)vinyl]-3-hydroxyphenyl 2-aminoacetate hydrochloride, 9.

Novel compounds of this invention may be prepared by the following processes.

Compounds represented by 1, 2 and 3 may be prepared by Wittig-Horner reaction. Substituted benzyl phosphonate may be reacted with methoxy substituted benzaldehyde in the presence of sodium hydride. Demethylation may be effected by treating with pyridine hydrochloride resulting in compounds 1, 2 and 3. This reaction scheme is shown hereinafter.

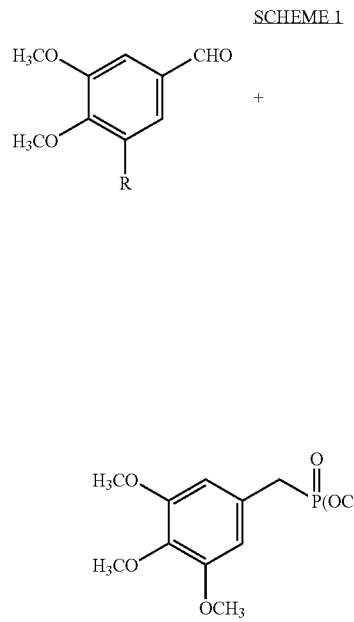

SCHEME 1

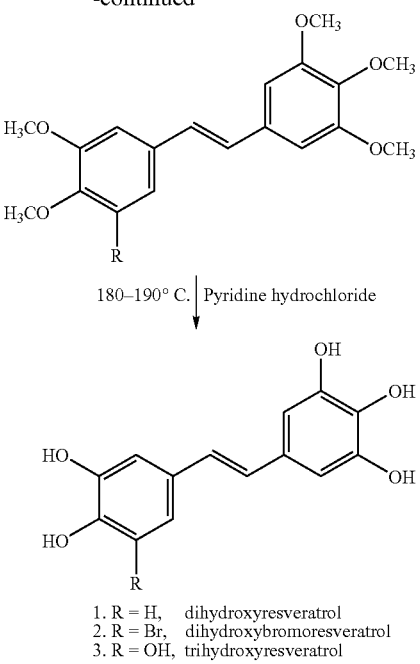

1. R = H, dihydroxyresveratrol
2. R = Br, dihydroxybromoresveratrol
3. R = OH, trihydroxyresveratrol Compounds represented by 4, 5, 6, 7, 8 and 9 may be prepared by 1,3-dicyclohexylcarbodiimide coupling of protected resveratrol, with corresponding acids or alkyl halides. The condensation product is subjected to debenzylation in the presence of aluminium chloride to produce compounds indicated by 4, 5, 6, 7, 8 and 9. This reaction is represented by the reaction scheme 2 shown below.

SCHEME 2

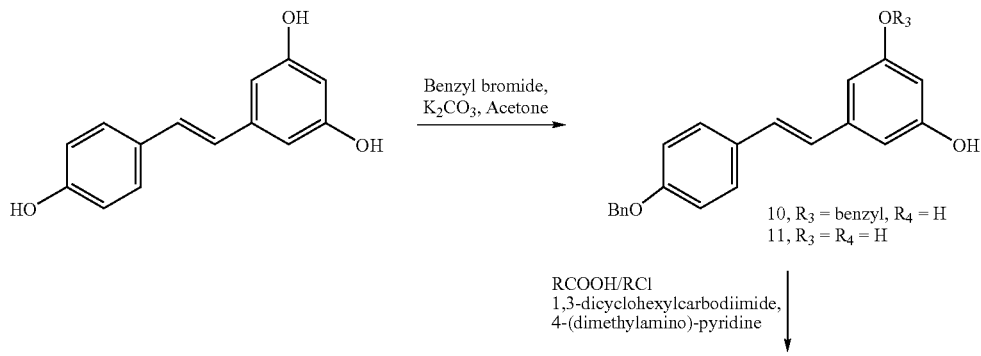

10, R₃ = benzyl, R₄ = H
11, R₃ = R₄ = H

RCOOH/RCl
1,3-dicyclohexylcarbodiimide,
4-(dimethylamino)-pyridine

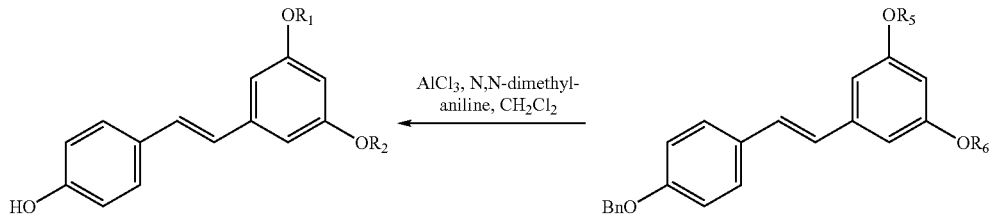

4  $R_1 = H$, $R_2 = $ 3,4,5-trihydroxybenzoyl
5  $R_1 = R_2 = $ 3,4,5-trihydroxybenzoyl
6  $R_1 = H$, $R_2 = $ 3,4-dihydroxycinnamoyl
7  $R_1 = H$, $R_2 = $ 3,4,5-trihydroxycinnamoyl
8  $R_1 = H$, $R_2 = $ —CH$_2$CH$_2$N(CH$_3$)$_2$
9  $R_1 = H$, $R_2 = $ —OCCH$_2$NH$_2$·HCl 12  $R_6 = $ 3,4,5-tribenzyloxybenzoyl, $R_5 = $ benzyl
13  $R_5 = R_6 = $ 3,4,5-tribenzyloxybenzoyl
14  $R_6 = $ 3,4-dibenzyloxycinnamoyl, $R_5 = $ benzyl
15  $R_6 = $ 3,4,5-tribenzyloxycinnamoyl, $R_5 = $ benzyl
16  $R_6 = $ —CH$_2$CH$_2$N(CH$_3$)$_2$, $R_5 = $ benzyl
17  $R_6 = $ —OCCH$_2$NHBOC, $R_5 = $ benzyl The final product obtained has the following substituents from the reaction scheme 2 as shown below:

4. $R_1$=H, $R_2$=3,4,5-trihydroxybenzoyl;
5. $R_1$=$R_2$=3,4,5-trihydroxybenzoyl;
6. $R_1$=H, $R_2$=3,4-dihydroxycinnamoyl;
7. $R_1$=H, $R_2$=3,4,5-trihydroxycinnamoyl;
8. $R_1$=H, $R_2$=—CH$_2$CH$_2$N(CH$_3$)$_2$;
9. $R_1$=H, $R_2$=—COCH$_2$NH$_2$.HCl This invention also includes processes for preparing novel resveratrol analogs.

One such process comprises subjecting diethyl 3,4,5-trimethoxybenzylphosphonate with 3,4-dimethoxybenzaldehyde or 5-bromo-3,4-dimethoxybenzaldehyde or 3,4,5-trimethoxybenzaldehyde in presence of NaH to give 1-(3,4-dimethoxyphenyl)-2-(3,4,5-trimethoxyphenyl)ethylene or 1-(5-bromo-3,4-dimethoxyphenyl)2-(3,4,5-trimethoxyphenyl)ethylene or 1,2-bis(3,4,5-trimethoxyphenyl)ethylene. These compounds may be demethylated in the presence of pyridine hydrochloride to get analogs of resveratrol shown as compounds of 1, 2 and 3.

Preferred embodiments relating to the different processes of preparing resveratrol analogs of the subject invention are illustrated in the examples given below.

EXAMPLE: 1

5-[(1E)-2-(3,4,5-trihydroxphenyl)vinyl]-benzene1,2,3-triol, 3

To an ice cold solution of sodium hydride (0.57 g, 12 mmol) in dry tetrahydrofuran (10 mL) was added 3,4,5-trimethoxybenzylphosphonate ester (3.2 g, 10 mmol) in THF (5 mL) via syringe for 15 min. The solution was slowly allowed to rt and stirred for 15 min. After cooling the solution was added 3,4,5-trimethoxybenzaldehyde (1.3 g, 7 mmol) in THF (5 mL) and stirred at ice cold temperature for 2 hrs and at rt for 2 hrs. Methanol (2 mL) was added to destroy the excess sodium hydride, diluted with ice cold water and acidified with dil HCl. The solution was extracted with chloroform and the organic layer was washed with water, sodium bicarbonate, brine and dried over sodium sulfate. The residue obtained after evaporation of the solvent was chromatographed over silica gel column to give 1,2-bis(3,4,5-trimethoxyphenyl) ethylene, m.p. 218–220° C.; IR (KBr) $v_{max}$ 2931, 2827, 1586, 1506, 1454, 1247, 1121, 987, 824 cm$^{-1}$; $^1$H NMR (CDCl$_3$, 400 MHz) δ 6.94 (2H, s), 6.74 (4H, s), 3.92 (12H, s), 3.87 (6H, s).

Demethylation: A mixture of 1,2-bis(3,4,5-trimethoxyphenyl) ethylene (1.0 g) and pyridine hydrochloride (5.0 g) was heated with stirring at 180–190° C. for 4 hrs. After cooling to room temperature the reaction mixture was diluted with ice water, acidified with dil HCl and extracted with ethyl acetate thrice. The combined ethyl acetate layer was washed with water, brine and dried over sodium sulfate. The residue obtained after evaporation of the solvent was chromatographed over silica gel column eluting with chloroform-methanol to give 3, m.p. 242–244° C.; IR (KBr) $v_{max}$ 3466, 1614, 1531, 1318, 1179, 1013, 956, 830 cm$^{-1}$; $^1$H NMR (CH$_3$OD, 400 MHz) δ 6.47 (2H, s), 6.32 (4H, s).

EXAMPLE: 2

5-[(1E)-2-(3,4-dihydroxyphenyl)vinyl]-benzene1,2,3-triol, 1

Reaction of diethyl 3,4,5-trimethoxybenzylphosphonate (5.4 g, 17 mmol) with 3,4-dimethoxybenzaldehyde (2 g, 12 mmol) in presence of NaH (0.97 g, 20 mmol), under the conditions noted in example 1, gave 1-(3,4-dimethoxyphenyl)-2-(3,4,5-trimethoxyphenyl) ethylene, m.p. 150–152° C.; IR (KBr) $v_{max}$ 2934, 2835, 1583, 1510, 1331, 1249, 1125, 1024, 1004, 976, 850 cm$^{-1}$; $^1$H NMR (CDCl$_3$, 400 MHz) δ 7.06 (1H, s), 7.05 (1H, dd, J=8.0, 1.9 Hz), 6.97 (1H, d, J=16.0 Hz), 6.89 (1H, d, J=16.0 Hz), 6.87 (1H, d, J=8.0 Hz), 6.73 (2H, s), 3.95 (3H, s), 3.92 (6H, s), 3.91 (3H, s), 3.87 (3H, s).

Demethylation: The 1-(3,4-dimethoxyphenyl)-2-(3,4,5-trimethoxyphenyl) ethylene (1.3 g) on demethylation with pyridine hydrochloride (7 g) under the conditions noted in example 1 gave 1, pp. 222–224° C.; IR (KBr) $v_{max}$ 3450, 3338, 1608, 1535, 1449, 1320, 1177, 1119, 1035, 956, 848, 797 cm$^{-1}$; $^1$H NMR (CH$_3$OD, 400 MHz) δ 6.76 (1H, s), 6.61 (1H, d, J=8.0 Hz), 6.55 (1H, d, J=16.0 Hz), 6.54 (1H, d, J=8.0 Hz), 6.50 (1H, d, J=16.0 Hz), 6.33 (2H, s).

EXAMPLE: 3

5-[(1E)-2-(5-Bromo-3,4-dihydroxyphenyl)vinyl]-benzene1,2,3-triol, 2

Reaction of diethyl 3,4,5-trimethoxybenzylphosphonate (2.7 g, 8 mmol) with 5 bromo-3,4-dimethoxybenzaldehyde (1.5 g, 6 mmol) in presence of NaH (0.5 g, 10 mmol) under the conditions noted in example 1, gave 1-(5-bromo-3,4-dimethoxyphenyl)-2-(3,4,5-trimethoxyphenyl) ethylene, m.p. 180–182° C.; IR (KBr) $v_{max}$ 3000, 2939, 1582, 1555, 1509, 1492, 1418, 1347, 1277, 1249, 1126, 1044, 998, 962, 840 cm$^{-1}$; $^1$H NMR (CDCl$_3$, 400 MHz) δ 7.30 (1H, d, J=1.8 Hz), 6.97 (1H, d, J=1.8 Hz), 6.95 (1H, d, J=16.2 Hz), 6.87 (1H, d, J=16.2 Hz), 6.72 (2H, s), 3.93 (3H, s), 3.92 (6H, s), 3.87 (6H, s).

Demethylation: The 1-(5-bromo-3,4-dimethoxyphenyl)-2-(3,4,5-trimethoxyphenyl) ethylene (1.3 g) on demethylation with pyridine hydrochloride (7 g) under the conditions noted in example 1 gave 2, m.p. 148° C.; IR (KBr) $v_{max}$ 3450, 1610, 1536, 1461, 1431, 1340, 1291, 1191, 1038, 997, 954, 842, 799 cm$^{-1}$; $^1$H NMR (DMSO-d$_6$, 400 MHz) δ 9.81 (1H, s), 9.21 (1H, s), 8.88 (2H, s), 8.30 (1H, s), 7.13 (1H, s), 6.93 (1H, s), 6.72 (1H, d, J=16.2 Hz), 6.64 (1H, d, J=16.2 Hz), 6.47 (2H, s).

EXAMPLE: 4

5-[(1E)-2-(4-hydroxyphenyl)vinyl]-3-hydroxyphenyl 3,4,5-trihydroxybenzoate, 4.

3,4'-Dibenzyloxyresveratrol (10): To a mixture of resveratrol (5.0 g, 22 mmol), potassium carbonate (12.5 g, 91 mmol) in acetone (100 mL) was added benzyl bromide (5.5 mL, 46 mmol) and the mixture was stirred at rt for 14 hr. The solids were filtered off and the solvent was removed under reduced pressure. The residue obtained was chromatographed over silica gel column eluting with a mixture of pet. ether-ethyl acetate (80:20), gave 10 (2.2 g, 25%), which was recrystallised from chloroform-hexane, m.p. 144–146° C.; IR (Neat) $v_{max}$ 3376, 1595, 1505, 1445, 1257, 1153, 1019, 963, 835, 771 cm$^{-1}$.

1-(Tribenzyloxybenzoyl)-3,4'-dibenzyloxyresveratrol (12): To a solution of dibenzyloxyresveratrol (10, 0.5 g, 1.23 mmol) in dichloromethane (25 mL) were added sequentially 3,4,5-tribenzyloxybenzoic acid (0.645 g, 1.47 mmol), DMAP (catalytic) and then DCC (0.5 g, 2.45 mmol) at rt. The reaction mixture was stirred at the same temperature for 14 hrs and the solid was filtered. The solution was diluted with chloroform and washed with water, 2% aq. acetic acid, 1% sodium bicarbonate, brine and dried over sodium sulfate. The residue obtained after evaporation of the solvent was chromatographed over silica gel column eluting with chloroform-hexane, gave 12 (0.9 g, 90%), m.p. 158–160° C.; IR (Neat) $v_{max}$ 2925, 1731, 1594, 1504, 1434, 1332, 1237, 1194, 1123, 1021, 743, 699 cm$^{-1}$.

1-O-Galloylresveratrol (4): To a mixture of 1-(tribenzyloxybenzoyl)-3,4'-dibenzyloxyresveratrol (12, 0.5 g, 0.6 mmol), N,N,-dimethylaniline (3.2 mL, 25 mmol) and CH$_2$Cl$_2$ (25 mL), was added aluminium chloride (1.8 g, 13.5 mmol) at 0–5° C. and the reaction mixture was slowly brought to rt and stirred at rt for 6 h. The reaction mixture was quenched with 1N HCl (25 mL) and extracted with ethyl acetate (2×25 mL). The combined organic layer was washed with water, brine and dried over sodium sulfate. The residue obtained after removal of the solvent was purified by column chromatography over silica gel column using mixtures of chloroform-methanol (90:10) as eluent to give 4 (110 mg, 48%), which was crystallised from chloroform-methanol, m.p. 254–256° C., IR (KBr) $v_{max}$ 3410, 1700, 1612, 1449, 1378, 1235, 1144, 1038 cm$^{-1}$; $^1$H NMR (CH$_3$OD, 400 MHz) δ 7.21(2H, d, J=7.75 Hz), 7.03 (2H, d, J=8.88 (1H, d, J=16.25 Hz), 6.72 (1H, d, J=16.28 Hz), 6.67 (1H, s), 6.62 (1H, s), 6.60 (2H, d, J=8.29 Hz), 6.30 (1H, s).

EXAMPLE: 5

3-[(1E)-2-(4-hydroxyphenyl)vinyl]-5-(3,4,5-trihydroxyphenylcarbonyloxy)-phenyl 3,4,5-trihydroxybenzoate, 5

1,3-Di-(tribenzyloxybenzoyl)-4'-benzyloxyresveratrol (13): Reaction of monobenzyloxy resveratrol (11, 0.5 g, 1.57 mmol), with 3,4,5-tribenzyloxybenzoic acid (1.66 g, 3.77 mmol), in the presence of DMAP (catalytic) and DCC (1.29 g, 6.28 mmol) under the conditions noted in example 4 gave 13 (1.4 g, 77%), m.p. 180–182° C.; IR (KBr) $v_{max}$ 3031, 1732, 1590, 1505, 1428, 1381, 1333, 1188, 1122, 1003, 859, 748, 696 cm$^{-1}$.

1,3-O-Digalloylresveratrol (5): Reaction of 1,3-di-(tribenzyloxybenzoyl)-4'-benzyloxyresveratrol (13, 1.4 g, 1.2 mmol) with N,N,-dimethylaniline (6.4 mL, 50 mmol) and aluminium chloride (4.8 g, 36 mmol) under the conditions noted in example 4 gave 5 (100 mg, 16%), which was crystallised from chloroform-methanol, m.p. 210–212° C., IR (KBr) $v_{max}$ 3404, 1710, 1606, 1514, 1453, 1383, 1350, 1202, 1129, 1041, 997, 953, 753 cm$^{-1}$; $^1$H NMR (CH$_3$OD, 400 MHz) δ 7.35 (2H, d, J=8.5 Hz), 7.18 (1H, s), 7.17 (1H, s), 7.14 (4H, s), 7.10 (1H, d, J=16.0 Hz), 6.93 (1H, d, J=16.0 Hz), 6.81–6.83 (1H, m), 6.70 (2H, d, J=8.5 Hz).

EXAMPLE: 6

5-[(1E)-2-(4-hydroxyphenyl)vinyl]-3-hydroxyphenyl (2E)-3-(3,4-dihydroxyphenyl) prop-2-enoate, 6

1-(3,4-Dibenzyloxycinnamoyl)-3,4'-dibenzyloxyresveratrol (14):

Reaction of dibenzyloxy resveratrol (10, 0.2 g, 0.49 mmol) with 3,4-dibenzyloxycinnamic acid (0.212 g, 0.59 mmol) in presence of DMAP (catalytic) and DCC (0.2 g, 0.98 mmol) under the conditions noted in example 4 gave 14 (0.32 g, 87%), m.p. 122–124° C.; IR (Neat) $v_{max}$ 3032, 2926, 1724, 1630, 1599, 1510, 1453, 1383, 1250, 1133, 1022, 843, 736, 697 cm$^{-1}$.

1-O-(3,4-Dihydroxycinnamoyl) resveratrol (6): Reaction of 1-(3,4-dibenzyloxycinnamoyl)-3,4'-dibenzyloxyresveratrol (14, 0.3 g, 0.4 mmol) with N,N,-dimethylaniline (2 mL, 1.8 mmol) and aluminium chloride (1.2 g, 9.0 mmol) under the conditions noted in example 4 gave 6 (55 mg, 35%), which was crystallised from chloroform-methanol, m.p. 216–220° C., IR (KBr) $v_{max}$ 3338, 1709, 1637, 1602, 1514, 1384, 1277, 1173, 1152, 982, 961, 846 cm$^{-1}$; $^1$H NMR (DMSO-d$_6$, 400 MHz) δ 9.74 (2H, s, Ar—OH), 9.62 (1H, s, Ar—OH), 9.23 (1H, s, Ar—OH), 7.68 (1H, d, J=15.9 Hz), 7.43(2H, d, J=8.1 Hz), 7.14 (1H, d, J=8.0 Hz), 7.12 (1H, d, J=8.0 Hz), 7.11 (1H, d, J=16.2 Hz), 6.94 (1H, d, J=16.2 Hz), 6.82 (2H, s), 6.80 (1H, s), 6.78 (2H, d, J=8.0 Hz), 6.50 (1H, d, J=15.9 Hz), 6.45 (1H, s).

EXAMPLE: 7

5-[(1E)-2-(4-hydroxyphenyl)vinyl]-3-hydroxyphenyl (2E)-3-(3,4,5-trihydroxyphenyl) prop-2-enoate, 7

1-(3,4,5-Tribenzyloxycinnamoyl)-3,4'-dibenzyloxyresveratrol (15): Reaction of dibenzyloxyresveratrol (10, 0.5 g, 1.23 mmol) with 3,4,5-tribenzyloxycinnamic acid (0.69 g, 1.47 mmol) in presence of DMAP (catalytic) and DCC (0.5 g, 2.45 mmol) under the conditions noted in example 4, gave 15 (0.8 g, 76%), m.p. 130–132° C. ; IR (Neat) $v_{max}$ 3032, 2929, 1726, 1630, 1582, 1506, 1432, 1382, 1271, 1246, 1136, 1027, 827, 737, 697 cm$^{-1}$.

1-O-(3,4,5-Trihydroxycinnamoyl)resveratrol (7): Reaction of 1-(3,4,5-tribenzyloxycinnamoyl)-3,4'-dibenzyloxyresveratrol (15, 0.75 g, 0.88 mmol) with N,N,-dimethylaniline (5.0 mL, 40 mmol) and aluminium chloride (3.0 g, 22 mmol) under the conditions noted in example 4, gave 7 (150 mg, 42%), which was crystallised from chloroform-methanol, m.p. 210–212° C., IR (KBr) $v_{max}$ 3366, 1711, 1635, 1603, 1515, 1449, 1292, 1172, 1149, 1031, 995, 963, 835 cm$^{-1}$; $^{1}$H NMR (DMSO-d$_6$, 400 MHz) δ 9.75 (1H, s, Ar—OH), 9.63 (1H, s, Ar—OH), 9.22 (2H, s, Ar—OH), 8.94 (1H, s, Ar—OH), 7.59 (1H, d, J=15.8 Hz), 7.43 (2H, d, J=8.5 Hz), 7.11 (1H, d, J=16.4 Hz), 6.94 (1H, d, J=16.4 Hz), 6.8 (1H, s), 6.82 (1H, s), 6.77 (2H, d, J=8.4 Hz), 6.70 (2H, s), 6.44 (1H, s), 6.39 (1H, d, J=15.8 Hz).

EXAMPLE: 8

3-[(1E)-2-(4-hydroxyphenyl)vinyl]-5-[2-(dimethylamino)ethoxy] phenol, 8

1-(N,N-Dimethylaminoethyl)-3,4'-dibenzyloxyresveratrol (16): To a solution of dibenzyloxy resveratrol (10, 0.5 g, 1.23 mmol) in acetone (50 mL) were added sequentially, potassium carbonate (0.85 g, 6.13 mmol) and N,N-dimethyl aminoethyl HCl (0.36 g, 2.45 mmol) at rt. The reaction mixture was refluxed for 5 hrs. The solids were filtered and the residue obtained after evaporation of the solvent was chromatographed over silica gel column eluting with 5% chloroform-methanol, gave 16 (0.5 g, 85%); IR (Neat) $v_{max}$ 3064, 3031, 2936, 1595, 1510, 1453, 1297, 1248, 1162, 1054, 962, 832, 741, 698 cm$^{-1}$.

1-O-(N,N-Dimethyl aminoethyl) resveratrol (8): Reaction of 1-(N,N-dimethyl aminoethyl)-3,4'-dibenzyloxyresveratrol (16, 0.6 g, 1.25 mmol) with N,N,-dimethylaniline (1.0 mL) and aluminium chloride (0.7 g, 5.0 mmol) under the conditions noted in example 4, gave 8 (110 mg, 29%), which was crystallised from chloroform-methanol, m.p. 92–94° C., IR (KBr) $v_{max}$ 3410, 2927, 1587, 1512, 1455, 1384, 1267, 1166, 1016, 962, 837 cm$^{-1}$; $^{1}$H NMR (DMSO-d$_6$, 400 MHz) δ 9.58 (1H, br s, Ar—OH), 9.41 (1H, br s, Ar—OH), 7.41 (2H, d, J=8.5 Hz), 7.05 (1H, d, J=16.3 Hz), 6.88 (1H, d, J=16.3 Hz), 6.77 (2H, d, J=8.5 Hz), 6.59 (1H, s), 6.53 (1H, s), 6.23 (1H, s), 4.04 (2H, t, J=5.7 Hz), 2.68 (2H, t, J=5.6 Hz), 2.26 (6H, s).

Antioxidant (superoxide scavenging) activity of these compounds are determined by conventional methods like McCord and Fridovich method, which is based on light induced superoxide generation by riboflavin and corresponding reduction of NBT. The assay mixture contains phosphate buffer, EDTA, NBT and riboflavin. Different concentrations of these compounds were assessed and their optical densities measured before and after illumination. The percentage value of inhibition of superoxide production by the compounds of this invention was evaluated and compared with the absorbance value of control and experimental data.

The compounds of this invention are found to show better bioprotective activity like superoxide scavenging (Table-I and FIG.-I; Superoxide scavenging activity is expressed in IC$_{50}$ values, lower the IC$_{50}$ value, higher is the activity).

Though the processes for preparation of the novel compounds of this invention have been disclosed hereinabove as specific embodiments, alternate processes known to persons skilled in the art are not excluded from the scope of this invention.

TABLE-I

| | Superoxide scavenging activity (NBT) | |
|---|---|---|
| S. No | Compound | IC$_{50}$ (μg/mL) |
| 1 | Resveratrol | 106.0 |
| 2 | 1 | 3.0 |
| 3 | 2 | 8.1 |
| 4 | 3 | 0.9 |
| 5 | 4 | 16.0 |
| 6 | 5 | 17.5 |
| 7 | 6 | 9.2 |
| 8 | 7 | 10.0 |
| 9 | 8 | 34.1 |
| 10 | 9 | 29.3 |

IC$_{50}$: 50% Inhibitory Concentration;
Lower the IC$_{50}$ value, higher is the antioxidant activity.

The invention claimed is:

1. A resveratrol analog of the general formula I:

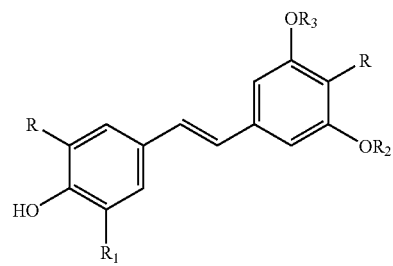

wherein;
1. R=OH and R$_1$=R$_2$=R$_3$=H;
2. R=OH, R$_1$=Br, and R$_2$=R$_3$=H;
3. R=R$_1$=OH and R$_2$=R$_3$=H;
4. R=R$_1$=R$_3$=H and R$_2$=3,4,5-trihydroxybenzoyl;
5. R=R$_1$=H and R$_2$=R$_3$=3,4,5-trihydroxybenzoyl;
6. R=R$_1$=R$_3$=H and R$_2$=3,4-dihydroxycinnamoyl;
7. R=R$_1$=R$_3$=H and R$_2$=3,4,5-trihydroxycinnamoyl;
8. R=R$_1$=R$_3$=H and R$_2$=—CH$_2$CH$_2$N(CH$_3$)$_2$; or
9. R=R$_1$=R$_3$=H and R$_2$=COCH$_2$NH$_2$HCL.

2. The resveratrol analog of the formula I, as claimed in claim 1, which is 5-[(1E)-2-(3,4-dihydroxyphenyl)vinyl]-benzene1,2,3-triol.

3. The resveratrol analog of the formula I, as claimed in claim 1, which is 5-[(1E)-2-(5-bromo-3,4-dihydroxyphenyl)vinyl]-benzene 1,2,3-triol.

4. The resveratrol analog of the formula I, as claimed in claim 1, which is 5-[(1E)-2-(3,4,5-trihydroxyphenyl)vinyl]-benzene1,2,3-triol.

5. The resveratrol analog of the formula I, as claimed in claim 1, which is 5-[(1E)-2-(4-hydroxyphenyl)vinyl]-3-hydroxyphenyl 3,4,5-trihydroxy-benzoate.

6. The resveratrol analog of the formula I, as claimed in claim 1, which is 3-[(1E)-2-(4-hydroxyphenyl)vinyl]-5-(3,4,5-trihydroxyphenylcarbonyloxy) phenyl 3,4,5-trihydroxy-benzoate.

7. The resveratrol analog, of the formula I, as claimed in claim 1, which is 5-[(1E)-2-(4-hydroxyphenyl)vinyl]-3-hydroxyphenyl (2E)-3-(3,4-dihydroxy-phenyl) prop-2-enoate.

8. The resveratrol analog, of the formula I, as claimed in claim 1, which is 5-[(1E)-2-(4-hydroxyphenyl)vinyl]-3-hydroxyphenyl (2E)-3-(3,4,5-trihydroxy-phenyl) prop-2-enoate.

9. The resveratrol analog of the formula I, as claimed in claim 1, which is 3-[(1E)-2-(4-hydroxyphenyl)vinyl]-5-[2-(dimethylamino)ethoxy] phenol.

10. The resveratrol analog of the formula I, as claimed in claim 1, which is 5-[(1E)-2-(4-hydroxyphenyl)vinyl]-3-hydroxyphenyl 2-aminoacetate hydrochloride.

11. A resveratrol analog of the general formula I as claimed in claim 1, wherein the analog is effective as an antioxidant.

12. A process for preparing a resveratrol analog of general formula I:

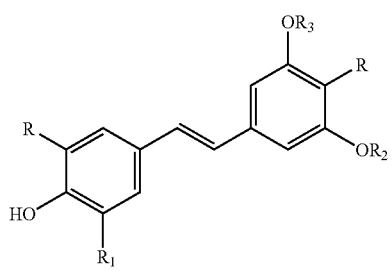

wherein:
  R is OH;
  $R_1$ is H, Br, or OH; and
  $R_2$ and $R_3$ are H; and
wherein the process comprises reacting substituted benzyl phosphonate with methoxy substituted benzaldehyde in the presence of sodium hydride and subsequent demethylation with pyridine hydrochloride.

13. A process for preparing a resveratrol analog of general formula I:

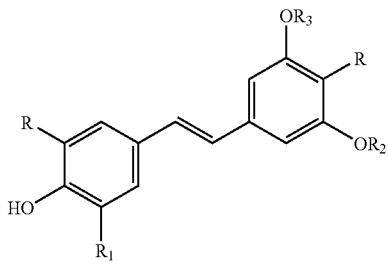

wherein:
  R and $R_1$ are H;
  $R_2$ is 3,4,5-trihydroxybenzoyl, —$CH_2CH_2N(CH_3)_2$, or —$COCH_2NH_2 \cdot HCL$; and
  $R_3$ is H or 3,4,5-trihydroxybenzoyl; and
wherein the process comprises coupling 1,3-dicyclohexylcarbodiimide with protected resveratrol, with corresponding acids or alkyl halides, and subjecting a condensation product obtained thereafter to debenzylation in the presence of aluminium chloride.

* * * * *